United States Patent [19]
Sakurai

[11] Patent Number: 6,019,775
[45] Date of Patent: Feb. 1, 2000

[54] ULTRASONIC OPERATION APPARATUS HAVING A COMMON APPARATUS BODY USABLE FOR DIFFERENT HANDPIECES

[75] Inventor: Tomohisa Sakurai, Sagamihara, Japan

[73] Assignee: Olympus Optical Co., Ltd., Tokyo, Japan

[21] Appl. No.: 09/103,367

[22] Filed: Jun. 23, 1998

[30] Foreign Application Priority Data

Jun. 26, 1997 [JP] Japan .................................. 9-170245

[51] Int. Cl.[7] .................................................. A61B 17/32
[52] U.S. Cl. ........................................... 606/169; 433/119
[58] Field of Search ............................. 606/169; 433/119

[56] References Cited

U.S. PATENT DOCUMENTS

5,076,276 12/1991 Sakurai et al. .
5,391,144 2/1995 Sakurai et al. .

Primary Examiner—Michael Buiz
Assistant Examiner—Jonathan D. Goldberg
Attorney, Agent, or Firm—Frishauf, Holtz, Goodman, Langer & Chick, P.C.

[57] ABSTRACT

An ultrasonic operation apparatus performs a treatment through the utilization of an ultrasonic oscillation and comprises a handpiece serving as a surgical tool and an apparatus body including a power source unit for supplying electric power to the handpiece. The handpiece is exchangeably attachable to, and detachable from, the apparatus body. The handpiece comprises an ultrasonic oscillation element for generating an ultrasonic oscillation, a probe for transmitting the ultrasonic oscillation which is generated from the ultrasonic oscillation element to a region of interest of a human being and a signal generating unit for generating a signal corresponding to a resonant frequency inherent in the ultrasonic oscillation element and hence the probe. The power source unit includes a power amplifying unit for receiving a signal corresponding to the resonant frequency inherent in the handpiece from the signal generation unit of the handpiece, amplifying the signal and generating a corresponding drive signal, and a connecting/transmitting unit for transmitting the corresponding drive signal which is generated at the power amplifying unit to the handpiece.

20 Claims, 4 Drawing Sheets

(PRIOR ART)

FIG. 8

(PRIOR ART)

FIG. 9

ULTRASONIC OPERATION APPARATUS HAVING A COMMON APPARATUS BODY USABLE FOR DIFFERENT HANDPIECES

BACKGROUND OF THE INVENTION

The present invention relates to an ultrasonic operation apparatus including a handpiece adapted to, for example, incise or emulsify a living tissue or destroy a stone in the living body.

In recent years, ultrasonic operation apparatuses have been used in more extensive fields beyond previously utilized fields, such as surgery on the liver having many blood vessels and brain surgery involving many nerve tissues. Heretofore, different kinds of ultrasonic operation apparatuses are proposed in accordance with their uses.

Figure 8:
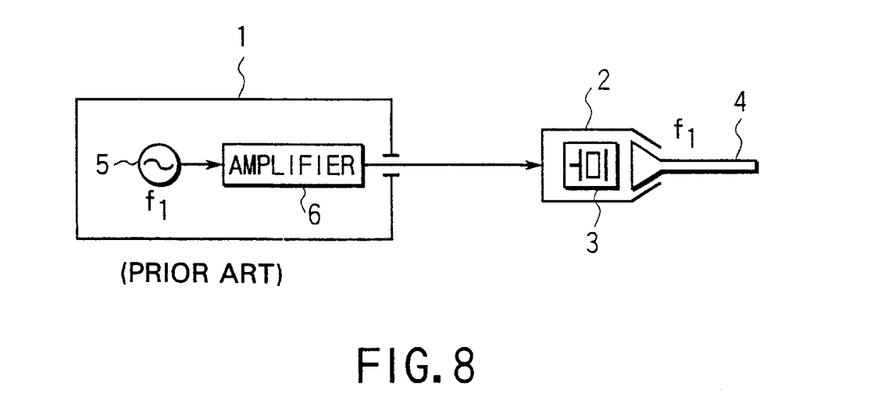
FIG. 8 is an explanatory view showing an arrangement of an ordinary ultrasonic operation apparatus.

FIG. 8 shows an arrangement of an ordinary ultrasonic operation apparatus. In FIG. 8, reference numeral 1 shows an apparatus body and reference number 2 shows a handpiece. An ultrasonic oscillation element 3 is incorporated in the handpiece 2. A probe 4 is connected to the ultrasonic oscillation element 3. The ultrasonic oscillation element 3 is of such a type as to oscillate with a resonant frequency f1. In this case, the apparatus body 1 includes an oscillator 5 adapted to oscillate with a frequency corresponding to the resonant frequency f1 and a power amplifier 6 adapted to amplify a frequency signal from the oscillator 5. That is, the oscillator 5 in the apparatus body 1 generates a drive signal corresponding to the resonant frequency f1 of the handpiece 2 and is so designed as to generate only a resonant frequency corresponding to the specific handpiece 2 of the apparatus.

Figure 9:
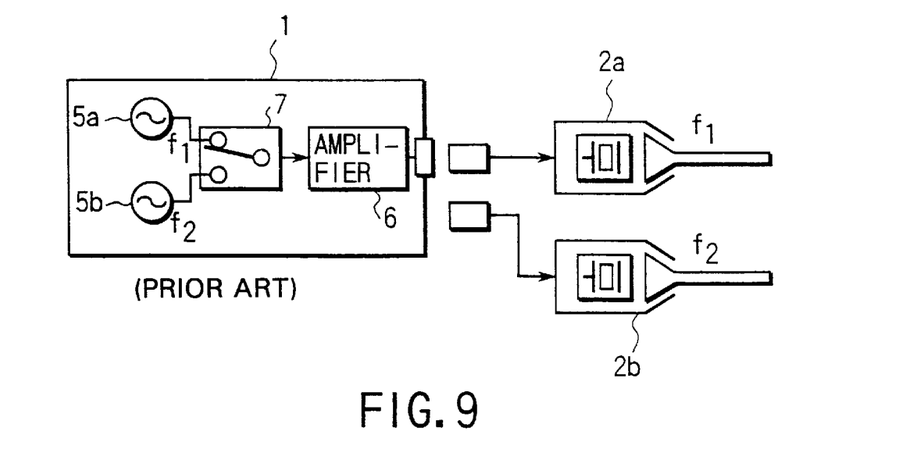
FIG. 9 is an explanatory view showing an arrangement of another ordinary ultrasonic operation apparatus.

FIG. 9 shows another conventional form of ultrasonic operation apparatus. This apparatus includes two kinds of handpieces 2a and 2b having, for example, 23 kHz and 35 kHz, respectively, the handpiece 2a oscillating with a resonant frequency f1 and the handpiece 2b oscillating with a resonant frequency f2. An apparatus body 1 includes two oscillators 5a and 5b adapted to generate drive signals corresponding to resonant frequencies f1 and f2 of the handpieces 2a and 2b and a switching means 7 adapted to switch one of these drive signals.

In this connection, it is to be noted that the oscillator 5 in the conventional ultrasonic operation apparatus is so designed as to generate only a resonant frequency corresponding to the specific handpiece 2 of the apparatus. For this reason, it is, therefore, necessary to prepare a specific apparatus body 1 corresponding to the handpiece 2 used.

If different variants as the handpiece 2 are provided in accordance with the uses to which they are put, it is necessary to prepare many more specific apparatus bodies in accordance with the these variant handpieces 2. In this respect, the conventional system has proved to be very uneconomical.

Although any one of the two kinds of handpieces 2a, 2b was able to be driven in the apparatus of such a type as to have two oscillators 5a and 5b for generating drive signals corresponding to resonant frequencies f1 and f2 of the handpieces 2a and 2b, it was not possible to use the apparatus body 1 for other types of handpieces.

Further, even in the case where an entirely new handpiece was developed, it was not possible to use the existing apparatus body on many occasions. If the kinds of handpieces are to be increased, it is necessary to improve the apparatus body and add a corresponding oscillator for generating a given frequency to the apparatus body. Such an improvement consumes more time and costs more money In addition, such an improvement is not very efficient.

If the oscillation frequency is low, it is possible to provide a larger-sized handpiece While, on the other hand, if a high oscillation frequency is used, it is possible to obtain a smaller-sized handpiece. That is, for a shorter wavelength it is possible to provide a smaller-sized handpiece and it is desirable to selectively use various kinds of handpieces depending upon the situation under which a surgery or operation is performed. As set out above, however, it is required that, in actual practice, a different apparatus including a power source unit be prepared, as a principle, for each handpiece and it is difficult to adopt this system in reality.

An associated conventional control circuit is comprised of an analog circuit. The analog circuit needs to be designed, taking into consideration a variation in manufacturing cost and in parameters caused by a variation in the environment. With recent advances in the digital techniques, digital processing has been adopted on various associated apparatuses. Even in this kind of ultrasonic operation apparatus, the ultrasonic oscillation element has the characteristic of possessing a mechanical resonance frequency and it has various frequencies in accordance with the designing of the probe and ultrasonic oscillation element.

In the case where, in order to prepare handpieces adaptable to various operations or surgeries, their mechanical dimension is varied, the resonant frequency varies in a delicate range. Even where designing is effected in such a delicate frequency range, if an associated circuit is constructed in the conventional analog type control system, then there are cases where it is difficult to effect control on the setting of the delicate frequency due to a variation in the environment, etc., at the driving of the handpiece involving a variation in a delicate frequency range. Even if there are more types of resonant frequencies involved, it has been difficult to readily handle the problem above by the associated apparatus.

BRIEF SUMMARY OF THE INVENTION

It is accordingly the object of the present invention to provide an ultrasonic operation apparatus which, even if handpieces of various resonant frequencies are developed or prepared, can readily use these handpieces on an associated common apparatus body without changing the apparatus body, and which can provide a drive device of high precision.

In order to achieve the above-mentioned object of the present invention, the first aspect of the present invention provides an ultrasonic operation apparatus for performing a treatment through the utilization of an ultrasonic oscillation, comprising a handpiece serving as a surgical tool and an apparatus body including a power source unit for supplying electric power to the handpiece, wherein the handpiece is exchangeably attachable to, and detachable from, the apparatus body and comprises an ultrasonic oscillation element for producing an ultrasonic oscillation, a probe for transmitting the ultrasonic oscillation which is produced from the ultrasonic oscillation element to a region of interest, and signal generating means for generating a signal corresponding to a resonant frequency inherent in the ultrasonic oscillation element and hence the probe; and the power source unit includes power amplifying means for receiving a signal corresponding to the resonant frequency inherent in the handpiece which is generated from the signal generating means of the handpiece, for amplifying the received signal and for generating a corresponding drive signal and connecting/transmitting means for transmitting the corresponding drive signal which is generated at the power amplifying means to the handpiece.

Further, the second aspect of the present invention provides a handpiece having a probe for producing an ultrasonic oscillation by an ultrasonic oscillation element and a handpiece having a connection section attachable to, and detachable from, an ultrasonic drive device for supplying a drive signal to the ultrasonic oscillation element, comprising:

signal generating means for generating a reference signal for providing a reference of the ultrasonic oscillation of the ultrasonic oscillation element;

a transmitting end provided on the connection section to transmit the reference signal to the ultrasonic drive device;

first transmitting means for transmitting the reference signal to the transmitting end;

a receiving end provided at the connection section to receive a drive signal generated by the ultrasonic drive device on the basis of the reference signal; and second transmitting means for transmitting the drive signal from the receiving end to the ultrasonic oscillation element.

Further, the third aspect of the present invention provides an ultrasonic drive device having a handpiece detachably connected thereto and producing an ultrasonic oscillation by the ultrasonic oscillation element, the ultrasonic drive device supplying a drive signal to the ultrasonic oscillation element, comprising:

an input terminal for receiving a reference signal for providing a reference of the ultrasonic oscillation of the ultrasonic oscillation element from an outside;

drive signal generation means for generating a drive signal on the basis of the reference signal;

first transmitting means for transmitting the reference signal to the drive signal generating means;

an output terminal for transmitting the drive signal to the ultrasonic oscillation element of the handpiece; and second transmitting means for transmitting the drive signal to the ultrasonic oscillation element.

Further, a fourth aspect of the present invention provides a handpiece having a probe for producing an ultrasonic oscillation by the ultrasonic oscillation element and a connection device located relative to an ultrasonic drive device for supplying a drive signal to the ultrasonic oscillating element to detachably connect the handpiece and the ultrasonic drive device, comprising:

signal generation means for generating a reference signal for providing a reference of the ultrasonic oscillation of the ultrasonic oscillation element;

a transmitting end connectable to an input terminal of the ultrasonic drive device to transmit the reference signal to the ultrasonic drive device;

first transmitting means for transmitting the reference signal to the transmitting end;

a receiving end connectable to an output terminal of the ultrasonic drive device to receive a drive signal generated by the ultrasonic drive device on the basis of the reference signal; and second transmitting means provided on the ultrasonic oscillation element side to transmit the drive signal from the receiving end to the ultrasonic oscillation element.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments give below, serve to explain the principles of the invention.

DETAILED DESCRIPTION OF THE INVENTION

The embodiments of the present invention will be explained below with reference to accompanying drawing.

(First Embodiment)

Figure 1:
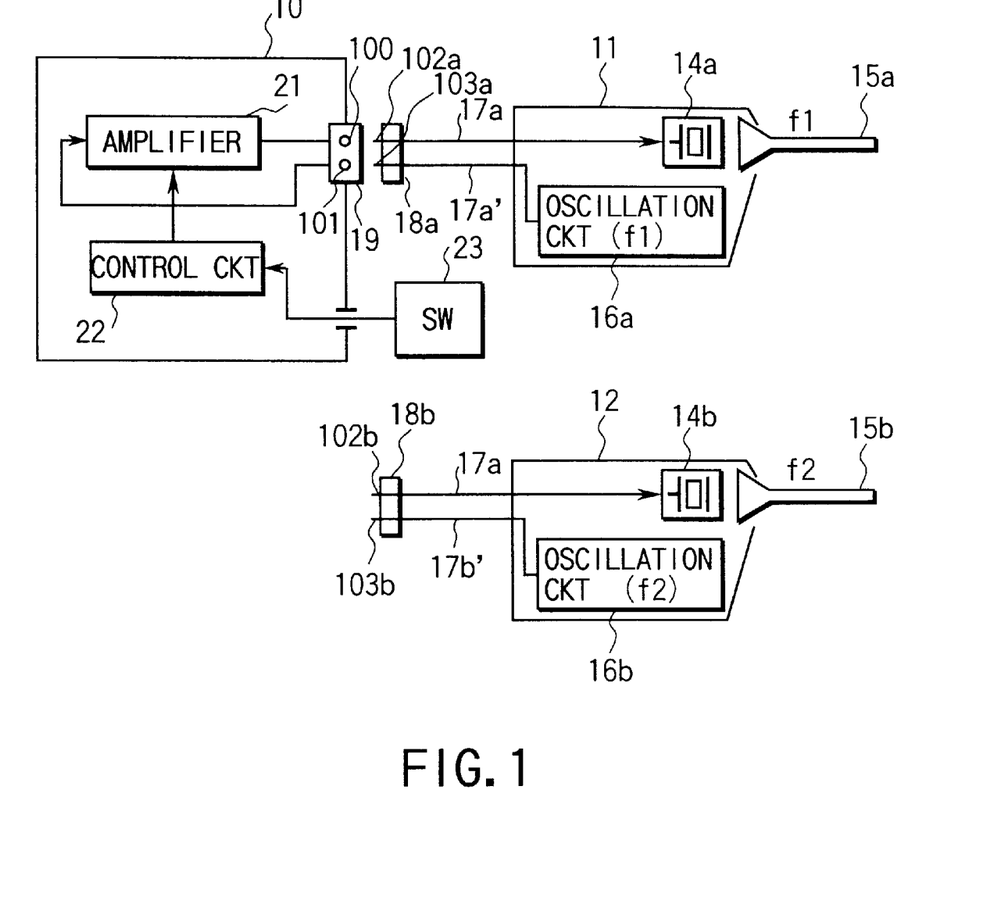
FIG. 1 is an explanatory view showing an ultrasonic operation apparatus according to a first embodiment of the present invention.

FIG. 1 is an explanatory view for explaining an ultrasonic operation apparatus according to a first embodiment of the present invention.

The ultrasonic operation apparatus comprises an apparatus body 10 serving also as a power source unit and a handpiece 11 or 12. The respective handpieces 11 and 12 can be connected to the apparatus body 10 by a connection means as will be set out below.

The first handpiece 11 includes an ultrasonic oscillation element 14a and a probe 15a connected to the ultrasonic oscillation element 14a. The first handpiece 11 is of such a type that, with a resonant frequency of the ultrasonic oscillation element 14a and hence a probe 15a given as f1, an oscillation circuit (signal generating means) 16a is provided as an oscillation circuit for generating a high frequency signal of a corresponding frequency f1.

A connection cord (first transmitting means) 17a' is connected at one end to an oscillation circuit 16a in the first handpiece 11 and at the other end to a connector (connection section) 18a. The connector 18a has a transmitting end 103a for transmitting a high frequency signal from the oscillation circuit 16a. Further, a connection cord (second transmitting means) 17a is connected at one end to the ultrasonic oscillation element 14a in the first handpiece 11 and at the other hand to the connector (connection section) 18a. The connector 18a has a receiving end 102a for receiving a signal from a power amplifier as will be set out below.

The second handpiece 12 includes an ultrasonic oscillation element 14b and a probe 15b connected to the ultrasonic oscillation element 14b. The second handpiece 12 is of such a type that, with a resonance frequency of the ultrasonic oscillation element 14b and hence the probe 15b given as f2, an oscillation circuit (signal generating means) 16b serves as an oscillator for generating a high frequency signal of a corresponding frequency f2.

A connector cord (first transmitting means) 17b' is connected at one end to an oscillation circuit 16b in the second handpiece 12 and at the other hand to a connector (connection section) 18b. The connector 18b has a transmitting terminal 103b for transmitting a high frequency signal from the oscillation circuit 16b. A connection cord (second transmitting means) 17b is connected at one end to the ultrasonic oscillation element 14b in the second handpiece 12 and at the other end to the connector (connection section) 18b. The connector 18b has a receiving end 102b for receiving a signal from the power amplifier as will be set out below.

On the other hand, the apparatus body 10 includes a power amplifier 21 serving as a power amplifying means and a control circuit 22. Further, the apparatus body 10 has a socket 19 serving as a connecting/transmitting means having an input terminal 101 and an output terminal 100. Further, a foot switch 23 is connected to the apparatus body 10 and serves as an operating means for rendering an output of the power amplifier 21 on or off.

The first handpiece 11 can be connected to the apparatus body 10 by connecting the connector 18a to the apparatus body 10. Similarly, the second handpiece 12 can be connected to the apparatus body 10 by connecting the connector 18b to the socket 19 of the apparatus body 10. Further, in addition to the first and second handpieces 11 and 12 it is also possible to use another handpiece, not shown, for exchange.

In the arrangement above, when the foot switch 23 is turned ON, for example, with the first handpiece 11 selected and the connector 18a connected to the socket 19 of the apparatus body 10, then an ON signal is transmitted to the control circuit 22 to enable the power amplifier 21 to be driven. An oscillation signal of the frequency f1 from the oscillator 16a is input through the transmitting end 103a of the connector 18a to the power amplifier 21 in the apparatus body 10 where it is amplified. An output from the power amplifier 21 is supplied through a receiving end 102a of the connector 18a to the ultrasonic oscillation element 14a in the handpiece 11. At that time, the ultrasonic oscillation element 14a is driven, so that an oscillation of a resonant frequency f1 appears from the probe 15a.

When, on the other hand, the foot switch 23 is turned ON, for example, with the second handpiece 12 selected and the connector 18b connected to the socket 19 of the apparatus body 10, then under control of the control circuit 22 an oscillation signal of a frequency f2 from the oscillator circuit 16b is amplified by the power amplifier 21 and a corresponding output is supplied to the ultrasonic oscillation element 14b in the second handpiece 12. At that time, the ultrasonic oscillation element 14b is driven, so that an oscillation of a resonant frequency f2 emerges from the probe 15b.

By doing so, the same apparatus body 10 can be used directly for those different handpieces 11 and 12 and it is not necessary to change the apparatus body 10. Further, the apparatus can also be used for those handpieces other than the handpieces 11 and 12.

As set out above, since the oscillation circuits 16a and 16b are provided, as oscillation sources, in the handpieces 11 and 12, respectively, so as to generate high-frequency signals corresponding to their own resonant frequencies, it is possible to design these handpieces at any free frequency. Therefore, it is not necessary to change the "apparatus body" side in principle. It is much expected that the apparatus body 10 finds a wider application. In the case where a new handpiece is designed/developed, an oscillation circuit of a corresponding resonant frequency can be incorporated into the handpiece and it is possible to develop a handpiece of every associated frequency. In this connection the oscillation circuit (16a, 16b), which is able to be constructed as a very small IC unit, is never a bulky circuit.

Further, as the transmitting means for connecting the apparatus body 10 to the handpieces 11, 12, it is only necessary to provide at least three lines, that is, one for the signal line of the oscillation circuit 16a (16b), one for the output line of the power amplifier 21 and one for a common line. Even if the oscillation circuit 16a (16b) is driven from the "apparatus body" side, it is sufficient to add a power source line, so that an adequate form of a standard is ensured.

(Second Embodiment)

Figure 2:
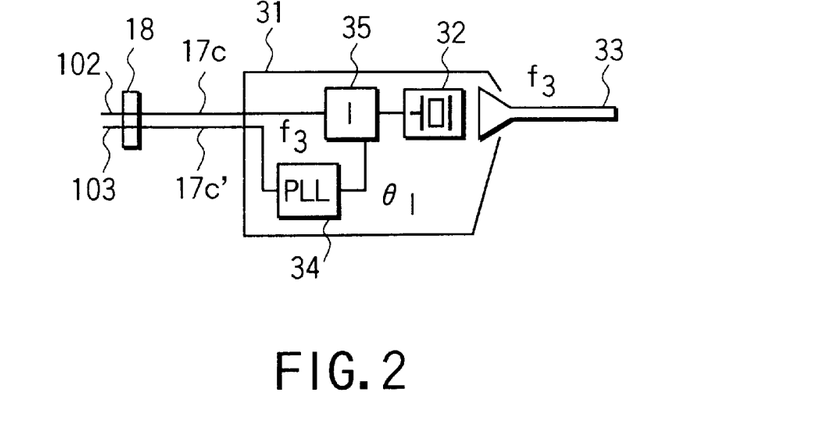
FIG. 2 is an explanatory view showing an ultrasonic operation apparatus according to a second embodiment of the present invention.

FIG. 2 is an explanatory view showing a handpiece 31 according to a second embodiment of the present invention. An ultrasonic oscillation element 32 is incorporated into a handpiece 31 and a probe 33 in the handpiece is connected to the ultrasonic oscillation element 32. The ultrasonic oscillation element 32, and hence the probe 33, is adapted to oscillate at its frequency f3. A phase locked loop (PLL) circuit 34 and current detection section 35 are provided in the handpiece 31.

A connection cord (first transmitting means )17c' is connected at one end to the PLL circuit 34 in the handpiece 31 and at the other end to a connector (connection section) 18. The connector 18 has a transmitting end 103 for transmitting a high-frequency signal from the PLL circuit 34. A connection cord (second transmitting means) 17c is connected at one end to the current detection section 35 in the handpiece 31 and at the other end to the connector (connection section) 18. The connector 18 has a receiving end 102 for receiving a signal from a power amplifier 21.

The PLL circuit 34 provides an oscillation circuit for tracking the resonant frequency f3 and generating a signal of a frequency corresponding to the resonant frequency f3. A current phase signal detected at the current detection section 35 is sent to the PLL circuit 34 and, through the PLL circuit 34, a drive signal flowing through the ultrasonic oscillation element 32 has its voltage current phase θI set to a zero degree. The handpiece 31 is substantially the same as that of the first embodiment except at such a portion of the oscillation circuit. In this embodiment, a plurality of kinds of handpieces 31 can be used as in the case of the first embodiment by being connected to the apparatus body 10.

(Third Embodiment)

Figure 3:
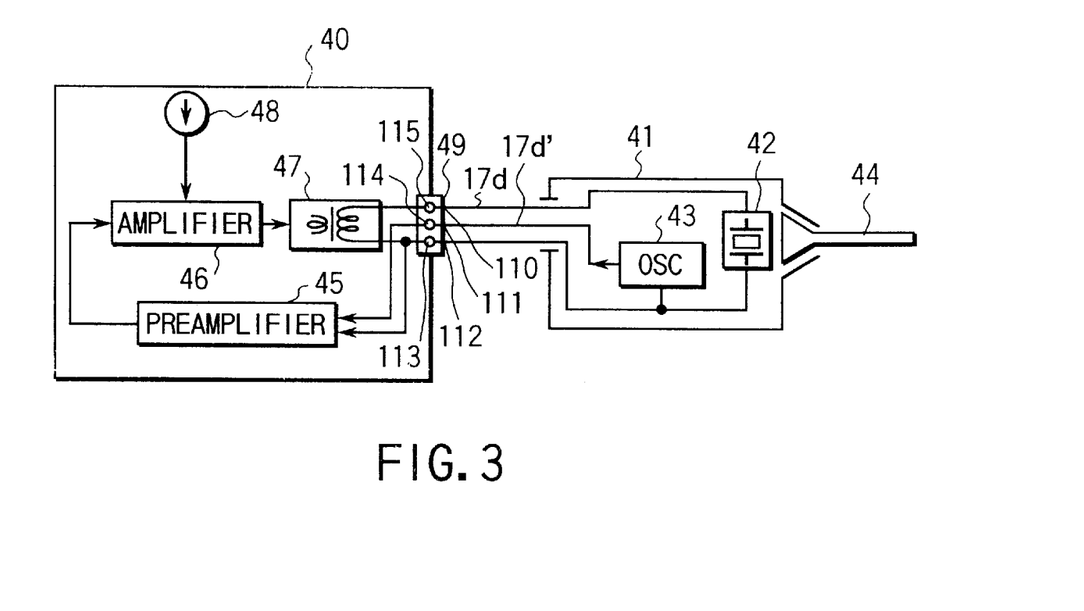
FIG. 3 is an explanatory view showing an ultrasonic operation apparatus according to a third embodiment of the present invention.

FIG. 3 is an explanatory view showing an ultrasonic operation apparatus according to a third embodiment of the present embodiment. In the third embodiment, a handpiece 41 includes an ultrasonic oscillation element 42 and oscillation circuit (signal generating means) 43. A probe 44 is connected to the ultrasonic oscillation element 42 and the oscillation circuit 43 has an oscillation frequency which differs according to the kind of handpiece 41.

A connection cord (first transmitting means) 17d' is connected at one end to the oscillation circuit 43 and at the other end to a connector, not shown. The connector has a transmitting end 111 for transmitting a high-frequency signal from the oscillation circuit 43. Further, a connection cord (second transmitting means) 17d is connected at one end to the ultrasonic oscillation circuit 42 in the handpiece 41 and at the other end to the connector. The connector further has a receiving end 110 for receiving a signal from a transformer as will be set out below and ground 112.

The apparatus body 40 includes a preamplifier 45 for pre-amplifying a signal from the oscillation circuit 43 in the handpiece 41, a power amplifier 46 for amplifying an output from the preamplifier 45, and the transformer 47 for delivering an output of the power amplifier 45. The apparatus body 114 is equipped with a socket 49 serving as a connecting/transmitting means having an input terminal 114, an output terminal 115 and ground 113. FIG. 3 shows a state in which the transmitting end 111 of the connector is connected to the input terminal 114, the receiving end 110 of the connector is connected to the output terminal 115, and the ground 112 of the connector is connected to the ground 113.

The above-mentioned power amplifier 46 is equipped with a constant current source 48, so that it is possible to obtain a steady output at a predetermined amplitude and hence to drive the ultrasonic oscillation element 42 by a steady drive signal of a given amplitude. A plurality of kinds of handpieces 41 are detachably connected to the apparatus body 40 through the same connecting/transmitting means 49 as in the first embodiment.

(Fourth embodiment)

Figure 4:
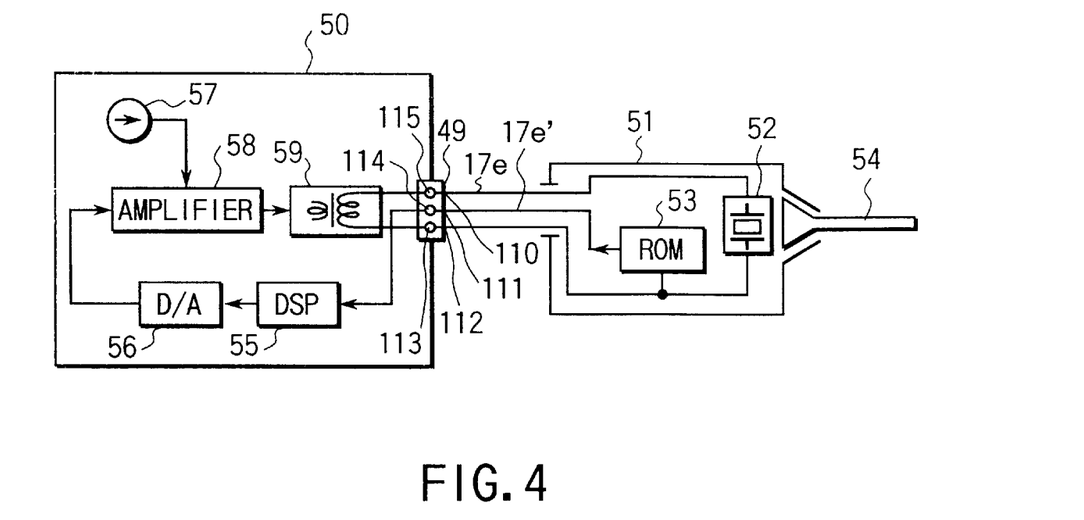
FIG. 4 is an explanatory view showing an ultrasonic operation apparatus according to a fourth embodiment of the present invention.

FIG. 4 is an explanatory view showing an ultrasonic operation apparatus according to a fourth embodiment of the present invention. The present embodiment includes a handpiece 51 having an ultrasonic oscillation element 52 and a ROM (signal generating means) 53, the ultrasonic oscillation element 52 being connected to a probe 54. A connection cord (first transmitting means) 17e' is connected at one end to the ROM 53 and at the other end to a connector, not shown. The connector has a transmitting end 111 for transmitting a signal from the ROM 53. Further, a connection cord (second transmitting means) 17e is connected at one end to the ultrasonic oscillation element 52 and at the other end to the connector, not shown. The connector above has a receiving end 110 for receiving a signal from a transformer as will be set out below and ground 112.

A control body 50 includes a digital signal processor (DSP) 55 for receiving a signal from the ROM 53 on the handpiece 51 side and D/A converter 56 for converting a digital output of the DSP 55 to an analog signal and, further includes, as in the third embodiment, the power amplifier 58 equipped with a constant current source 57 and the above-mentioned transformer 59 for allowing an output of the power amplifier 58 to be delivered. The apparatus body 50 also includes a socket 49 serving as a connecting/transmitting means having an input terminal 114, an output terminal 115 and ground 113. FIG. 4 shows a state in which the connector is connected at its transmitting end 111 to an input terminal 114, at its receiving end 110 to an output terminal 115 and at its ground 112 to the ground 113. The handpiece 51 can be attached/detached to/from the apparatus body 50 by a connecting/transmitting means 49 similar to that of the above-mentioned embodiment.

In the above-mentioned embodiment, data on a resonant frequency determined by the ultrasonic oscillation element 52 is sent to the apparatus body 50 side from the ROM 53 in the handpiece 51 and, after being signal-processed by the DSP 55 on the basis of the data, sent to the D/A converter 56 where an intended frequency signal is generated. The signal is amplified by the power amplifier 58 and a corresponding drive signal of a given steady amplitude is supplied through the output transformer 59 to the handpiece 51. By doing so, the apparatus body 50 serves as a programmable digital oscillator and it is possible to obtain signals of various frequencies in a simpler way by rewriting the information in the ROM 53 in the handpiece 51.

In the fourth embodiment, the ROM 53 is used as a sharing component and, even if the ultrasonic oscillation element 52 has its frequency varied by being design-modified, it is possible to cope with this situation, by rewriting the data in the ROM 53, and to lower a manufacturing cost through the common use of the component part. Since the data is digitized, even if the handpiece 51 is sterilized by autoclaving, etc., there occurs no variation of a constant and it is possible to supply steady data over a prolonged period of time and hence to realize a handpiece 51 strong enough to be used under a varying environment.

In the case where mechanical dimensions are varied in order to secure handpieces adaptable to various medical treatments, the resonant frequency varies over a delicate range, but, because the associated circuit is constructed under a digital type control system, even if there exists a delicate frequency variation, it is not difficult to have the setting of such a delicate frequency controlled under a varying environmental condition at a time of driving the handpiece.

(Fifth Embodiment)

Figure 5:
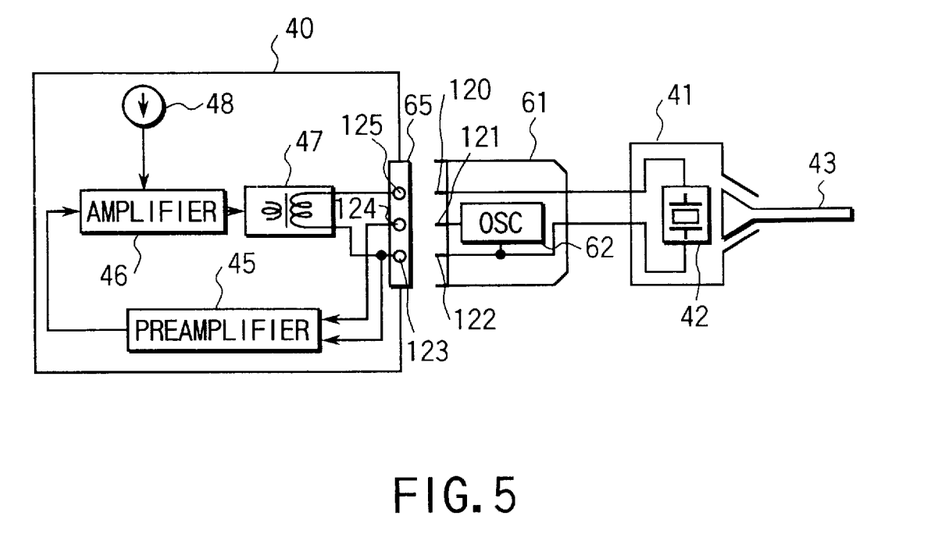
FIG. 5 is an explanatory view showing an ultrasonic operation apparatus according to a fifth embodiment of the invention.

FIG. 5 is an explanatory view showing an ultrasonic operation apparatus according to a fifth embodiment of the present invention.

The fifth embodiment is of such a type as to provide an oscillation source (signal generating means) 62 in a connector 61 connected to a connection cord of a handpiece 41 in the third embodiment. The connector 61 has a transmitting end 121 for transmitting a signal from its oscillation source 62, a receiving end 120 for receiving a signal from a later-described transformer and ground 122.

The apparatus 40 includes a socket 65 having an input terminal 124, an output terminal 125 and ground 123 and serving as a connecting/transmitting means. The input terminal 124 is connectable to the transmitting end 121 of the connector 61, the output terminal 125 is connectable to the receiving end 120 and the ground 123 is connectable to the ground 122. The apparatus body 40 includes a constant current source 48, a power amplifier 46, the transformer 47 and a preamplifier 45.

By such an arrangement, instead of providing the oscillation circuit 62, memory means, ROM, etc., in a body section of a handpiece 41, these circuit elements for instance may be included in the connector 61. In this case, even if, technically, the shapes of the oscillation circuit and ROM are greater, the size of the body section of the handpiece 41 can be made the same as that of the connectional counterpart and it is possible to secure the heretofore mentioned advantage of the present invention without adversely affecting an operability.

Since the handpiece 41 has its oscillation circuit means and memory means for instance incorporated relative to the connector means connected to the device body (40, 50) serving as a power source unit, the portion of the connector (61, 63) allows some shape or configuration variation and it is much easier to achieve this embodiment.

Figure 6:
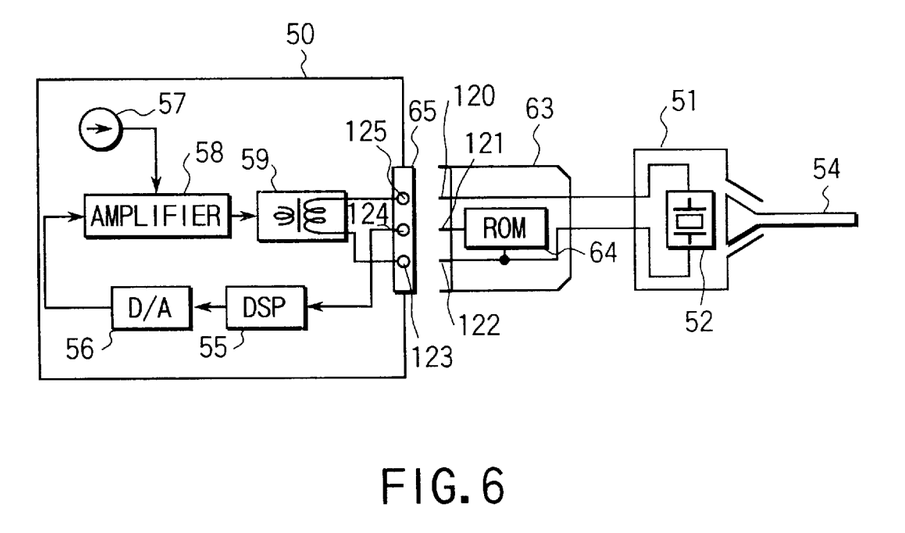
FIG. 6 is an explanatory view showing a variant of the ultrasonic operation apparatus of FIG. 5.

A variant of the fifth embodiment is of such a type that, as shown in FIG. 6, a ROM (signal generating means) 64 is provided in the connector 63 of a connection cord of the handpiece 51 of the fourth embodiment. In FIG. 6, the connector 63 has a transmitting end 121 for transmitting a signal from a ROM 64, a receiving end 120 for receiving a signal from a later-described transformer and ground 122.

Further, the apparatus body 50 includes a constant current source 57, a power amplifier 58, a D/A converter 56, DSP 55 and the above-mentioned transformer 59. Further, the apparatus body 50 includes a socket 66 serving as a connecting/transmitting means having an input terminal 124, an output terminal 125 and ground 123. The input terminal 124 is connectable to the transmitting end 121 of the connector 63, the output terminal 125 is connectable to the receiving end 120 and the ground 123 is connectable to the ground 122. In the arrangement shown, it is possible to obtain the same advantage as that in the arrangement of FIG. 5.

(Sixth Embodiment)

Figure 7:
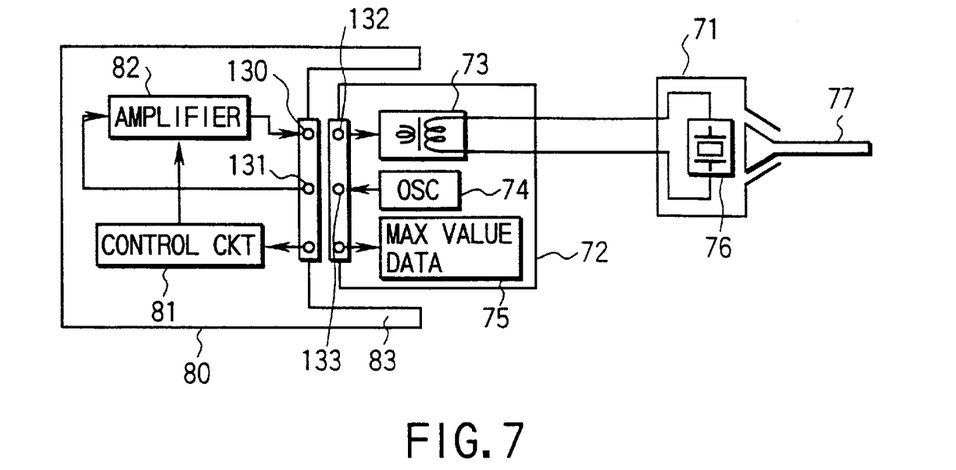
FIG. 7 is an explanatory view showing an ultrasonic operation apparatus according to a sixth embodiment of the present invention.

FIG. 7 is an explanatory view showing an ultrasonic operation apparatus according to a sixth embodiment of the present embodiment. In the embodiment above, a connector 72 is connected to a connection cord of a handpiece 71 and characterized in that it has an output transformer 73, an oscillation circuit (signal generating means) 74 and a data storing means 75 for storing different data for different handpieces. On the other hand, an ultrasonic oscillation element 76 and probe 77 connected to the ultrasonic oscillation element 76 are provided at the body section of the handpiece 71.

The connector 72 includes a transmitting end 133 for transmitting a signal from its oscillation circuit 74 and a receiving end 132 for receiving a signal from a later-described amplifier.

An apparatus body 80 includes a control circuit 81 and the above-mentioned amplifier 82. In addition to these, it may also possible to provide other circuits. Further, the apparatus body 80 includes a socket 83 serving as a connecting/transmitting means having an input terminal 131 and an output terminal 130. The input terminal 131 is connectable to the transmitting end 133 and the output terminal 130 is connectable to the receiving end 132.

Here, the reason why data on the respective handpiece is stored in the data storing means 75 is as follows. First, the maximum value of electric current flowed therein differs depending upon the kinds of oscillators used (for example, ones having frequencies 23.5 kHz, 47 kHz, etc.). Secondly, in the case where the oscillator, even being of the same kind, is incorporated into a handpiece for surgical operation, a maximal current allowed to output a signal of a greater frequency is flowed in the associated circuit. In the case of a handpiece for blood tumor suction in brain surgery, however, the amplitude of the allowed maximal current may be about its half level and, hence, it is possible to set a current value of such a half level (when the set value of the apparatus is 100%). This is because it is necessary to have a different parameter (here the MAX value) for each handpiece.

It is to be noted that, in the case of connecting the connector 72 to the socket 83 of the apparatus body 80, an adaptor, not shown, may be used in which case the adaptor may include an output transformer 73, oscillation circuit 74, data storing means 75, etc.

As will be understood above, the data (parameters such as the MAX) relating to the handpiece 71 is stored in the connector 72 or adaptor and, by doing so, it is possible to identify the respective handpiece and hence to construct a more flexible system. Further, the apparatus body 80 can be constructed as a simple unit with some components shared.

In this connection it is to be noted that, since the turn ratio, configuration and frequency of the output transformer 73 differ in structure depending upon the structure of the handpiece, the output transformer 73 may be provided per handpiece 71.

As set out above, according to the present invention, the apparatus body can be used common among associated units and, even if various types of handpieces are sequentially developed, it is possible to use them on such a common apparatus body and to develop handpieces as proper successors more adaptable to a surgical tool. Further, the handpiece never includes any bulkier circuit such as a power amplifier and such a bulkier amplifier is provided on the power source unit side only, so that a compact handpiece can be realized and, in addition, a common power source unit can also be achieved relative to the handpiece. Further, the handpiece includes a generating means, such as an oscillation circuit, and, even if handpieces of various frequencies are developed, they can be driven simply through an exchange of handpieces, so that a useful system can be structured. A digital technique can also be used for the present apparatus and it is possible to provide an apparatus which operates stably in a digital environment.

Additional advantages and modifications will readily occurs to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

I claim:

1. An ultrasonic operation apparatus comprising a handpiece serving as a surgical tool and an apparatus body including a power source unit for supplying electric power to the handpiece, wherein:

the handpiece is exchangeably attachable to and detachable from the apparatus body, and comprises (i) an ultrasonic oscillation element for producing an ultrasonic oscillation, (ii) a probe for transmitting the ultrasonic oscillation to a region of interest, and (iii) signal outputting means for outputting a signal corresponding to an initial resonant frequency inherent in the ultrasonic oscillation element and hence the probe; and the power source unit includes (i) power amplifying means for receiving the signal output by the signal outputting means of the handpiece, for amplifying the received signal, and for generating a corresponding drive signal, and (ii) connecting/transmitting means for transmitting the corresponding drive signal to the handpiece.

2. An ultrasonic operation apparatus comprising a plurality of handpieces and an apparatus body including a common power source unit for supplying electric power to a given one of the handpieces which is connected to the apparatus body, wherein:

each of the handpieces is exchangeably attachable to and detachable from the apparatus body, and comprises (i) an ultrasonic oscillation element for producing an ultrasonic oscillation, (ii) a probe for transmitting the ultrasonic oscillation to a region of interest, and (iii) signal outputting means for outputting a signal corresponding to an initial resonant frequency inherent in the ultrasonic oscillation element and hence the probe; and the power source unit includes (i) power amplifying means for receiving the signal output by the signal outputting means of the given one of the handpieces which is connected to the apparatus body, for amplifying the received signal, and for generating a corresponding drive signal, and (ii) connecting/transmitting means for transmitting the corresponding drive signal to the given one of the handpieces which is connected to the apparatus body.

3. An ultrasonic operation apparatus comprising a plurality of handpieces and a common apparatus body including a power source unit for supplying electric power to a given one of the handpieces which is connected to the apparatus body, wherein:

each of the handpieces is exchangeably attachable to and detachable from the apparatus body, and comprises (i) an ultrasonic oscillation element for producing an ultrasonic oscillation, (ii) a probe for transmitting the ultrasonic oscillation to a region of interest, and (iii) an oscillation circuit for generating a signal corresponding to an initial resonant frequency inherent in the ultrasonic oscillation element and hence the probe; and the power source unit includes (i) power amplifying means for receiving the signal generated by the oscillation circuit of the given one of the handpieces which is connected to the apparatus body, for amplifying the received signal, and for generating a corresponding drive signal, and (ii) connecting/transmitting means for transmitting the corresponding drive signal to the given one of the handpieces which is connected to the apparatus body.

4. The ultrasonic operation apparatus according to claim 3, wherein the power source unit comprises means for supplying a constant current to drive the ultrasonic oscillation element of the given one of the handpieces which is connected to the apparatus body, so that a steady ultrasonic oscillation is effected without depending upon a variation in a load.

5. The ultrasonic operation apparatus according to claim 3, wherein the power amplifying means of the power source unit comprises a power amplifier having a frequency range of 20 kHz to 100 kHz.

6. The ultrasonic operation apparatus according to claim 3, wherein the oscillation circuit is incorporated in a connector connected between the handpiece and the power source unit.

7. An ultrasonic operation apparatus comprising a plurality of handpieces and a common apparatus body including a power source unit for supplying electric power to a given one of the handpieces which is connected to the apparatus body, wherein:

each of the handpieces is exchangeably attachable to and detachable from the apparatus body, and comprises (i) an ultrasonic oscillation element for producing an ultrasonic oscillation, (ii) a probe for transmitting the ultrasonic oscillation to a region of interest, and (iii) a PLL circuit for tracking a resonant frequency of the ultrasonic oscillation element and hence the probe based on an electric current supplied to the ultrasonic oscillation element, and for generating a signal corresponding to the tracked resonant frequency; and the power source unit includes (i) power amplifying means for receiving the signal output by the PLL circuit of the given one of the handpieces which is connected to the apparatus body, for amplifying the received signal, and for generating a corresponding drive signal, and (ii) connecting/transmitting means for transmitting the corresponding drive signal to the given one of the handpieces which is connected to the apparatus body.

8. An ultrasonic operation apparatus comprising a plurality of handpieces each serving as a surgical tool, and a common apparatus body including a power source unit for supplying electric power to a given one of the handpieces which is connected to the apparatus body, wherein:

each of the handpieces is exchangeably attachable to and detachable from the apparatus body, and includes (i) an ultrasonic oscillation element for producing an ultrasonic oscillation, (ii) a probe for transmitting the ultrasonic oscillation to a region of interest, and (iii) a memory for storing data relating to an inherent resonant frequency of the ultrasonic oscillation element and hence the probe; and the power source unit includes (i) a signal processor for generating a frequency signal based on the data stored with respect to the inherent resonant frequency of the ultrasonic oscillation element and hence the probe of the given one of the handpieces which is connected to the apparatus body, (ii) a power amplifying means for receiving the frequency signal and for amplifying the frequency signal, and (iii) connecting/transmitting means for transmitting a power signal corresponding to the amplified frequency signal to the given one of the handpieces which is connected to the apparatus body.

9. The ultrasonic operation apparatus according to claim 8, wherein the signal processor system is provided on a handpiece side of the power source unit.

10. The ultrasonic operation apparatus according to claim 8, wherein the memory is incorporated in a connector for connecting together the handpieces and the power source unit.

11. A handpiece having a probe which is ultrasonically oscillated by an ultrasonic oscillation element, and a connection section attachable to and detachable from an ultrasonic drive device for supplying a drive signal to the ultrasonic oscillation element, said handpiece comprising:

signal outputting means for outputting a reference signal corresponding to an initial resonant frequency of the ultrasonic oscillation element;

a transmitting end, provided at the connection section, for transmitting the reference signal to the ultrasonic drive device;

first transmitting means for transmitting the reference signal to the transmitting end;

a receiving end, connected to the connection section, for receiving a drive signal generated by the ultrasonic drive device based on the reference signal; and second transmitting means for transmitting the drive signal from the receiving end to the ultrasonic oscillation element.

12. The handpiece according to claim 11, wherein the reference signal has a frequency corresponding to the initial resonant frequency of the ultrasonic oscillation element and hence the probe.

13. The handpiece according to claim 11, wherein the signal outputting means comprises a ROM for generating a frequency corresponding to the initial resonant frequency of the ultrasonic oscillation element and hence the probe.

14. A handpiece having a probe which is ultrasonically oscillated by an ultrasonic oscillation element, and a connection section attachable to and detachable from an ultrasonic drive device for supplying a drive signal to the ultrasonic oscillation element, said handpiece comprising:

a PLL circuit for tracking a resonant frequency of the ultrasonic oscillation element and hence the probe based on an electric current supplied to the ultrasonic oscillation element, and for generating a reference signal corresponding to the tracked resonant frequency;

a transmitting end, provided at the connection section, for transmitting the reference signal to the ultrasonic drive device;

first transmitting means for transmitting the reference signal to the transmitting end;

a receiving end, connected to the connection section, for receiving a drive signal generated by the ultrasonic drive device based on the reference signal; and second transmitting means for transmitting the drive signal from the receiving end to the ultrasonic oscillation element.

15. An ultrasonic drive device which is detachably connectable to a handpiece having a probe and an ultrasonic oscillation element for driving the probe, said ultrasonic drive device comprising:

an input terminal for receiving, from an external source, a reference signal corresponding to an initial resonant frequency of the ultrasonic oscillation element of the handpiece;

drive signal generating means for generating a drive signal for driving the ultrasonic oscillation element of the handpiece based on the reference signal;

first transmitting means for transmitting the reference signal to the drive signal generating means;

an output terminal for transmitting the drive signal to the ultrasonic oscillation element of the handpiece; and second transmitting means for transmitting the drive signal to the ultrasonic oscillation element of the handpiece.

16. The ultrasonic drive device according to claim 15, further comprising insulating transmitting means provided between the drive signal generating means and the output terminal for transmitting the drive signal therebetween in an electrically insulated manner, without any electrical conduction.

17. A connection device for detachably connecting an ultrasonic drive device and a handpiece having a probe and an ultrasonic oscillation element for driving the probe, said connection device comprising:

signal outputting means for outputting a reference signal corresponding to an initial resonant frequency of the ultrasonic oscillation element of the handpiece;

a transmitting end connectable to an input terminal of the ultrasonic drive device for transmitting the reference signal to the ultrasonic drive device;

first transmitting means for transmitting the reference signal to the transmitting end;

a receiving end connectable to an output terminal of the ultrasonic drive device for receiving a drive signal for driving the ultrasonic oscillation element of the handpiece, said drive signal being generated by the ultrasonic drive device based on the reference signal; and second transmitting means, provided on the ultrasonic oscillation element side, for transmitting the drive signal from the receiving end to the ultrasonic oscillation element.

18. The connection device according to claim 17, wherein the reference signal has a frequency corresponding to the initial resonant frequency of the ultrasonic oscillation element and hence the probe.

19. The connection device according to claim 17, wherein the signal generation means includes a ROM for generating a frequency corresponding to the initial resonant frequency of the ultrasonic oscillation element and hence the probe.

20. The connection device according to claim 17, further comprising insulating transmitting means provided between the receiving end and the second transmitting means for transmitting the drive signal therebetween in an electrically insulated manner, without any electrical conduction.

* * * * *

UNITED STATES PATENT AND TRADEMARK OFFICE
CERTIFICATE OF CORRECTION

PATENT NO. : 6,019,775
DATED : February 1, 2000
INVENTOR(S) : Tomohisa Sakurai

It is certified that error appears in the above-identified patent and that said Letters Patent is hereby corrected as shown below:

<u>Title page,</u>
Item [56], References Cited, under "U.S. PATENT DOCUMENTS" insert
-- 3,809,977    5/74    Balamuth et al
   5,425,704    6/95    Sakurai et al
   5,668,235   11/74   Sakurai et al --.

Signed and Sealed this

Nineteenth Day of March, 2002

Attest:

JAMES E. ROGAN
*Director of the United States Patent and Trademark Office*

*Attesting Officer*